United States Patent [19] [11] 4,322,314
Onoda et al. [45] Mar. 30, 1982

[54] PROCESS FOR SEPARATING COBALT COMPONENT FROM HYDROESTERIFICATION REACTION MIXTURE

[75] Inventors: Takeru Onoda, Tokyo; Keisuke Wada, Yokohama; Hironori Kageyama; Hideki Yamanouchi, both of Tokyo; Kenji Karube, Toride, all of Japan

[73] Assignees: Mitsubishi Chemical Ind.; Lion Corporation, both of Tokyo, Japan

[21] Appl. No.: 128,149

[22] Filed: Mar. 7, 1980

[30] Foreign Application Priority Data

Apr. 21, 1979 [JP] Japan .................................. 54-49475

[51] Int. Cl.³ .................... B01J 31/40; C01G 59/02; C07C 67/38; C11C 3/02
[52] U.S. Cl. ................................ 252/412; 252/414; 252/420; 260/410.6; 260/410.7; 423/139; 560/233
[58] Field of Search ...................... 252/412, 414, 420; 423/139, 150; 560/233; 260/410.6, 410.7

[56] References Cited

U.S. PATENT DOCUMENTS 3,856,832 12/1974 Ethyl ........................... 260/410.9 R
3,974,194 8/1976 Isa et al. ........................ 260/410.6
4,041,057 8/1977 Fanning ...................... 260/410.9 R

FOREIGN PATENT DOCUMENTS 50-62888 5/1975 Japan .
52-22592 2/1977 Japan ................................... 252/420
52-62192 5/1977 Japan .
52-37999 9/1977 Japan .
53-37327 10/1978 Japan .

*Primary Examiner*—P. E. Konopka
*Attorney, Agent, or Firm*—Oblon, Fisher, Spivak, McClelland & Maier

[57] ABSTRACT

A cobalt component is separated from a hydroesterification reaction mixture obtained by reacting a polyhydric alcohol with an olefin and carbon monoxide in the presence of a cobalt carbonyl complex and a pyridine base, by contacting (a) pyridine or γ-picoline and (b) water with said reaction mixture containing the cobalt component and the product of a fatty acid ester of the polyhydric alcohol to separate it into two phases consisting of a phase containing the fatty acid ester of polyhydric alcohol and a phase containing a cobalt component.

In the process, the weight ratio of pyridine or γ-picoline to the product ester is 0.5 to 5 and the weight ratio of water to pyridine or γ-picoline is 0.05 to 10.

13 Claims, No Drawings

PROCESS FOR SEPARATING COBALT COMPONENT FROM HYDROESTERIFICATION REACTION MIXTURE

BACKGROUND OF THE INVENTION

1. Field of the Invention

The present invention relates to a process for separating a cobalt component from a hydroesterification reaction mixture. More particularly, it relates to a process for separating a cobalt component from a reaction mixture obtained by a reaction of a polyhydric alcohol with an olefin and carbon monoxide in the presence of a cobalt carbonyl complex and a pyridine base, thereby separating a fatty acid ester of a polyhydric alcohol in high efficiency.

2. Description of the Prior Arts

The principle process for producing fatty acid esters of polyhydric alcohols has recently changed from the conventional process employing natural fatty acids as starting materials to a total synthesis.

The process for producing fatty acid esters of polyhydric alcohol by reacting a polyhydric alcohol with an olefin and carbon monoxide in the presence of a cobalt carbonyl complex and a pyridine base such as pyridine, vinyl pyridines and alkyl pyridines has been disclosed in Japanese Examined Patent Publication Nos. 39810/1977 and 31128/1978. By this process, fatty acid esters of polyhydric alcohols can be obtained by mass production with lower cost compared to the conventional process. However it is indispensible to recover and reuse the catalyst metal in order to employ a homogeneous catalytic reaction as an industrial process.

The following processes have been proposed as processes for recovering the cobalt component from the reaction mixture obtained by the hydroesterification reaction using a cobalt carbonyl complex.

A liquid hydrocarbon is added to the reaction mixture obtained by the hydroesterification reaction using an excess of an alcohol, thereby separating a hydrocarbon phase containing the ester from an alcohol phase containing the cobalt carbonyl complex (Japanese Examined Patent Publication No. 47676/1976, U.S. Pat. No. 3,856,832).

A lower alcohol is added to the hydroesterification reaction mixture thereby extracting most of the cobalt carbonyl complex into a lower alcohol phase (Japanese Unexamined Patent Publication No. 62192/1977).

The hydroesterification reaction is carried out in a liquid paraffin having high boiling point and the reaction mixture is separated into a paraffin phase containing the ester and a phase containing the cobalt carbonyl complex. The ester is separated from the paraffin phase by distillation, and the phase containing the cobalt carbonyl complex is recycled into the reaction system in a continuous hydroesterification reaction (Japanese Examined Patent Publication No. 37327/1978).

However, all of these known processes have disadvantages. The first process can not be employed in the process for producing the full ester of a polyhydric alcohol since that would require excess of the olefin.

The second process has the disadvantage that a large quantity of the ester would be recycled together with the catalyst because the ester reaction product is partitioned at about same ratio between the two phases.

The third process has the advantage of recycling the catalyst in high efficiency but has the disadvantage of requiring larger equipment such as a reactor, a separator and a distillation tower, which cause a high fixed cost because a large quantity of paraffin is used as a solvent.

The inventors have developed a process for recovering the cobalt component and for separating and purifying a fatty acid ester of a polyhydric alcohol in an industrially advantageous manners in the process for producing the fatty acid ester of a polyhydric alcohol by the hydroesterification reaction using cobalt carbonyl complex as a catalyst. As a result, the process of the present invention has been accomplished.

SUMMARY OF THE INVENTION

It is an object of the present invention to provide a process for separating the cobalt component from a hydroesterification reaction mixture in high efficiency with low cost.

The foregoing and other objects of the present invention have been attained by contacting (a) pyridine or $\gamma$-picoline and (b) water with a hydroesterification reaction mixture containing a cobalt component and a fatty acid ester of a polyhydric alcohol which is obtained by a hydroesterification reaction of a polyhydric alcohol, an olefin and carbon monoxide in the presence of a cobalt carbonyl complex and a pyridine base, thereby separating the mixture into a phase containing the fatty acid ester of said polyhydric alcohol and a phase containing a cobalt component.

DETAILED DESCRIPTION OF THE PREFERRED EMBODIMENTS

The hydroesterification reaction of the present invention can be carried out under the following conditions.

A polyhydric alcohol, such as ethyleneglycol, neopentylglycol, glycerin, trimethylolpropane, pentaerythritol, dipentaerythritol or tripentaerythritol, is used with a $C_{3-30}$ olefin, preferably a $C_{4-12}$ straight chain olefin such as 1-butene, 1-pentene, 1-hexene, 1-heptene, 1-octene, 1-nonene, 1-decene, 2-pentene, 2-hexene, 2-heptene, 2-octene, 3-hexene or 3-heptene, at a ratio of 0.01 to 10 mole of the olefin to 1 equivalent of hydroxyl group of the polyhydric alcohol.

A cobalt component, such as cobalt carbonyl, hydrocobalt carbonyl or a cobalt carbonyl complex such as complexes obtained by substituting a part of the carbonyl ligands with a pyridine base (below-mentioned), is used at a ratio of 0.001 to 1 gram-atom of cobalt to 1 mole of the olefin.

A pyridine base, such as pyridine, 2-vinyl pyridine, 3-vinyl pyridine, 4-vinyl pyridine, 3-methyl-4-vinyl pyridine, $\alpha$-picoline, $\beta$-picoline, $\gamma$-picoline, 4-ethyl pyridine and 3,5-dimethyl pyridine, is used at a ratio of 1 to 100 mole to 1 gram-atom of the cobalt.

The hydroesterification reaction is carried out by reacting the polyhydric alcohol with the olefin and carbon monoxide in the presence of the cobalt component under a partial pressure of carbon monoxide of 10 to 250 kg/cm² at 70° to 250° C.

In accordance with the hydroesterification reaction, an ester of the polyhydric alcohol and a fatty acid having one more carbon atom than the olefin is mainly produced. In addition, small amounts of free fatty acid and aldehyde which have one more carbon atom than the olefin are produced by side-reactions.

The cobalt component is usually prepared by feeding into a catalyst activating column a salt of a fatty acid having one more carbon atom than the olefin and is activated with carbon monoxide or a water gas in the presence of a pyridine base under a pressure of about 150 to 250 kg/cm$^2$ at about 150° to 200° C. to convert it into the cobalt carbonyl complex. It is then fed into the reaction system. Therefore, the free fatty acid exists at a stoichiometrically excess ratio to the cobalt component in the reaction mixture, and when the cobalt carbonyl complex becomes unstable, a cobalt ion becomes bonded to the fatty acid to form a cobalt salt of the fatty acid.

Usually the stability of a cobalt carbonyl complex depends upon the partial pressure of carbon monoxide, the presence of a ligand such as pyridine base, and the temperature. When unreacted olefin or pyridine base is distilled off from the reaction mixture in the present invention, a part or whole of the cobalt carbonyl complex is decomposed to form the cobalt salt of the fatty acid.

The process of the present invention is carried out by contacting pyridine or γ-picoline and water with the hydroesterification reaction mixture containing the cobalt component, the pyridine base, the olefin and the fatty acid ester of the polyhydric alcohol (especially useful for fatty acid esters having a degree of esterification of more than 0.9) or by contacting pyridine or γ-picoline and water with a residue obtained by separating the olefin and/or the pyridine base from the reaction mixture. It is also possible to carry out the process of the invention by contacting pyridine or γ-picoline and water with a mixture obtained by adding $C_{3-30}$ olefin, preferably $C_{4-12}$ olefin and/or $C_{6-20}$ paraffin, to the hydroesterification reaction mixture or the residue obtained by separating the pyridine base from the hydroesterification reaction mixture.

It is also possible to carry out the process of the invention after treating the reaction mixture by aeration, such as bubbling oxygen or air, to convert the cobalt carbonyl complex into the cobalt salt of fatty acid.

The ratio of pyridine or γ-picoline is 0.2 to 10 parts by weight, preferably 0.5 to 5 parts by weight, to one part fatty acid ester as the product.

The ratio of water is 0.05 to 10 parts by weight, preferably 0.1 to 0.5 parts by weight, to one part pyridine or γ-picoline.

The hydroesterification reaction mixture, optionally after the above-mentioned treatments, can be treated in an atmosphere of an inert gas such as nitrogen or carbon monoxide or a water gas under the atmospheric pressure or higher pressure at the ambient temperature to 100° C. preferably with stirring for about 5 minutes to 2 hours.

If pyridine or γ-picoline is used as the pyridine base in the hydroesterification reaction, and if the quantity of pyridine or γ-picoline included in the reaction mixture is within the above-mentioned range, it is unnecessary to add an additional pyridine or γ-picoline, and it is possible to carry out the separation by adding only water at a desired ratio. When a pyridine base other than pyridine or γ-picoline is used in the hydroesterification reaction, it is preferable to remove such pyridine base from the reaction mixture by distillation, etc. before contacting pyridine or γ-picoline and water in order to prevent formation of a complicated system.

In accordance with the contact treatment, the mixture is easily separated into two phases, consisting of the phase containing the fatty acid ester of polyhydric alcohol as the upper phase and the phase containing the cobalt component as the lower phase.

The upper phase contains the fatty acid ester of the polyhydric alcohol, pyridine or γ-picoline, small amounts of water, the aldehyde, the fatty acid and sometimes the unreacted olefin. These impurities are separated by a distillation and the product is purified as desired to obtain the fatty acid ester of polyhydric alcohol having high purity.

The lower phase contains the cobalt component dissolved into a mixture of pyridine or γ-picoline and water. Therefore, it can be recycled as the recovered catalyst into the reaction system. However, it is preferable to activate a part of whole of the cobalt component by the above-mentioned catalyst activation step, after distilling pyridine or γ-picoline and water at any ratio if necessary, and to effectively reuse the activated catalyst by recycling into the reaction system.

The present invention will be further illustrated by certain examples and references which are provided for purposes of illustration only and are not intended to be limiting to the present invention.

EXAMPLE 1

One mol. of cobalt heptanoate, 7 mol. of pyridine and 1.5 mol. of water to 1 gram atom of cobalt were charged into an autoclave and were stirred at 180°–185° C. for 2 hours under a pressure of 200 kg/cm$^2$G with carbon monoxide to prepare an activated catalyst. Hydroesterification reaction was carried out by reacting 1 mol. of pentaerythritol, 8 mol. of 1-hexene and carbon monoxide in the presence of the above activated catalyst, with pyridine being present at a molar ratio of cobalt to pentaerythritol of 0.12 and pyridine to cobalt of 60. The reaction was carried out at a temperature of 185°–190° C. and under a pressure of 230 kg/cm$^2$G for 3.5 hours to obtain the reaction mixture of the following composition.

| Cobalt component | 4.88 mg as Co/ g-reaction mixture |
|---|---|
| Pentaerythritol heptanoate (degree of esterification of 0.98) | 38.3 wt. % |
| 1-Hexene | 17.6 wt. % |
| Pyridine | 34.0 wt. % |
| Heptanoic acid and heptanol | 7.5 wt. % |

To 45.3 g. of the reaction mixture were added 29.1 g of pyridine and 15.0 g of water. The mixture was stirred at 45° C. for 1 hour in nitrogen gas atmosphere and then kept at a standstill for 30 minutes to separated it into two phases. Each phase was separated and pentaerythritol heptanoate and the cobalt component were analyzed. As a result, the upper phase contained 97.4 wt.% of pentaerythritol heptanoate based on the total heptanoate whereas the lower phase contained 98.2 wt.% of the cobalt component based on the total cobalt component in the reaction mixture.

EXAMPLE 2

To 45.0 g. of the reaction mixture having the same composition used in Example 1 6.6 g of water was added. The mixture was stirred at 45° C. for 1 hour in nitrogen gas atmosphere and then kept at a standstill for 30 minutes to separate it into two phases. Each phase was separated and pentaerythritol heptanoate and the cobalt component were analyzed. As a result, 99.5 wt.% of pentaerythritol heptanoate was allotted in the upper phase and 89.8 wt.% of the cobalt component was allotted in the lower phase.

EXAMPLE 3

The reaction mixture having the same composition used in Example 1 was distilled under nitrogen gas at atmospheric pressure to separate a fraction distilling at 120° C. whereby the mixture having the following composition was obtained.

| Cobalt component | 7.10 mg as Co/ g-reaction mixture |
|---|---|
| Pentaerythritol heptanoate (degree of esterification of 0.98) | 55.8 wt. % |
| Pyridine | 29.5 wt. % |
| Heptanoic acid and heptanal | 10.9 wt. % |

To 24.5 g. of the mixture, 22.0 g. of pyridine and 9.6 g. of water were added. The mixture was stirred and separated into two phases as set forth in Example 1. As a result of the analyses, 95.4 wt.% of pentaerythritol heptanoate was allotted in the upper phase and 95.9 wt.% of the cobalt component was alloted in the lower phase.

EXAMPLE 4

In accordance with the process of Example 1, a reaction mixture containing 2.05 g. of pentaerythritol heptanoate (degree of esterification of 0.98) and 0.14 g. of cobalt heptanoate was produced, and 3.9 g. of pyridine and 1.2 g of water were added to the reaction mixture. The mixture was stirred at ambient temperature for 1 hour and then kept at a standstill for 30 minutes to separate it into two phases. The components were then analyzed. As a result, 84 wt.% of pentaerythritol heptanoate was allotted in the upper phase and 75 wt.% of cobalt heptanoate was allotted in the lower phase.

EXAMPLE 5

In accordance with the process of Example 1 a reaction mixture containing 1.96 g. of trimethylolpropane heptanoate (degree of esterification of 0.98) and 0.13 g. of cobalt heptanoate was produced, and 3.9 g. of pyridine and 1.2 g of water were added to the reaction mixture. The mixture was treated in the same manner as in Example 4 to separate it into two phases, and the components were analyzed. As a result, 96 wt.% of trimethylolpropane heptanoate was allotted in the upper phase and 51 wt.% of cobalt heptanoate was allotted in the lower phase.

EXAMPLE 6

In accordance with the process of Example 1, a reaction mixture containing 12.2 g. of dipentaerythritol heptanoate and 0.81 g. of cobalt heptanoate was produced, and 24.5 g. of pyridine and 7.3 g. of water were added to the reaction mixture. The mixture was stirred at an ambient temperature for 30 minutes and was kept at a standstill for 30 minutes to separate it into two phases after which the components were analyzed. As a result, 97.8 wt.% of dipentaerythritol heptanoate was allotted in the upper phase and 93.7 wt. % of cobalt heptanoate was allotted in the lower phase.

EXAMPLE 7

In accordance with the process of Example 1, a reaction mixture containing 20.0 g. of neopentylglycol heptanoate and 1.30 g. of cobalt heptanoate was produced, and 40.0 g. of pyridine and 12.0 g. of water were added to the reaction mixture. The mixture was stirred at an ambient temperature for 30 minutes and was kept at a standstill for 10 minutes to separate it into two phases after which the components were analyzed. As a result, 94.4 wt.% of neopentylglycol heptanoate was allotted in the upper phase and 94.6 wt.% of cobalt heptanoate was allotted in the lower phase.

EXAMPLE 8

In accordance with the process of Example 1, a reaction mixture containing 20.0 g. neopentylglycol pelargonate and 1.57 g. of cobalt pelargonate was produced, and 40.0 g. of pyridine and 12.0 g. of water were added to the reaction mixture. The mixture was treated in the same manner as in Example 7 to separate it into two phases and the components were analyzed. As a result, 99.2 wt.% of neopentylglycol pelargonate was allotted in the upper phase and 90.4 wt.% of cobalt pelargonate was allotted in the lower phase.

EXAMPLE 9

In accordance with the process of Example 1, a reaction mixture containing 20.0 g. of pentaerythritol heptanoate (a degree of esterification of 0.98) and 1.28 g. of cobalt heptanoate was produced, and 40.0 g. of γ-picoline and 13.4 g. of water were added to the reaction mixture. The mixture was treated in the same manner as in Example 7 to separate it into two phases, and the components were analyzed. As a result, 97 wt.% of pentaerythritol heptanoate was allotted in the upper phase and 97.1 wt.% of cobalt heptanoate was allotted in the lower phase.

EXAMPLE 10

In accordance with the process of Example 1, a hydroesterification reaction was carried out by reacting 1-hexene, pentaerythritol and carbon monoxide in the presence of cobalt catalyst and pyridine to obtain the reaction mixture of the following composition.

| Cobalt component | 4.6 mg as Co/ g-reaction mixture |
|---|---|
| Pentaerythritol heptanoate (degree of esterification of 0.95) | 38.0 wt. % |
| 1-Hexene | 21.9 wt. % |
| n-Hexane | 0.5 wt. % |
| Pyridine | 34.7 wt. % |
| Heptanoic acid and heptanal | 2.4 wt. % |

To 29.4 g. of the reaction mixture were added 6.6 g. of 1-hexene, 12.1 g. of pyridine and 6.7 g. of water. The mixture was stirred at 45° C. for 30 minutes in nitrogen gas atmosphere and then kept at a standstill for 10 minutes to separate it into two phases.

Each phase was separated and analyzed. As a result, about 100 wt.% of pentaerythritol heptanoate and 96.5% of 1-hexene and n-hexane were allotted in the upper phase, and 91.1 wt.% of the cobalt component was allotted in the lower phase.

EXAMPLE 11

Air was fed into the reaction mixture used in Example 10 at 60° C. for 1 hour. To 20.0 g. of the treated reaction mixture were added 6.0 g. of n-hexane and 8.7 g. of pyridine and 4.6 g. of water. The mixture was separated into two phases by the process set forth in Example 10. Each phase was separated and analyzed. As a result, 99.9 wt.% of pentaerythritol heptanoate and 88.0% of n-hexane and 1-hexene were allotted in the upper phase and 90.4 wt.% of the cobalt component was allotted in the lower phase.

What is claimed as new and intended to be covered by Letters Patent is:

1. A process for separating a cobalt component from a hydroesterification reaction mixture obtained by reacting a polyhydric alcohol with an olefin and carbon monoxide in the presence of a cobalt carbonyl complex and a pyridine base to give a fatty acid ester of said polyhydric alcohol, which comprises:

contacting (a) pyridine or γ-picoline and (b) water with said hydroesterification reaction mixture containing the cobalt component and said ester to separate said reaction mixture into two phases consisting of a phase containing said ester and a phase containing said cobalt component, wherein the weight ratio of pyridine or γ-picoline to said ester is 0.5 to 5 and the weight ratio of water to pyridine or γ-picoline is 0.05 to 10.

2. A process according to claim 1 wherein (a) pyridine or γ-picoline and (b) water are brought into contact with a residue obtained by separating unreacted olefin, pyridine base, or mixture of unreacted olefin and pyridine base from said hydroesterification reaction mixture.

3. A process according to claim 1 wherein (a) pyridine or γ-picoline and (b) water are brought into contact with a mixture obtained by adding a $C_{3-30}$ olefin to said hydroesterification reaction mixture or adding a $C_3$-$C_{30}$ olefin to a residue obtained by separating said pyridine base from said hydroesterification reaction mixture.

4. A process according to claim 1 wherein (a) pyridine or γ-picoline and (b) water are brought into contact with the hydroesterification reaction mixture after said reaction mixtures subjected to aeration.

5. A process according to claim 1 wherein (a) pyridine or γ-picoline and (b) water are brought into contact with a mixture obtained by adding a $C_{6-20}$ paraffin to said hydroesterification reaction mixture or adding a $C_{6-20}$ paraffin to a residue obtained by separating said pyridine base from said hydroesterification reaction mixture.

6. A process according to claim 1 wherein said hydroesterification reaction mixture is obtained by reacting said polyhydric alcohol and a $C_{3-30}$ olefin at a ratio of 0.01 to 10 mole of olefin to 1 equivalent of hydroxyl group of said polyhydric alcohol with carbon monoxide in the presence of said cobalt carbonyl complex at a ratio of 0.001 to 1 gram-atom Co to 1 mole of said olefin and 1 to 100 mole of said pyridine base to 1 gram-atom of cobalt.

7. A process according to claim 1 wherein said polyhydric alcohol is selected from the group consisting of ethyleneglycol, neopentylglycol, glycerin, trimethylolpropane, pentaerythritol, dipentaerythritol and tripentaerythritol.

8. A process according to claim 1 wherein said olefin is selected from the group consisting of 1-butene, 1-pentene, 1-hexene, 1-heptene, 1-octene, 1-nonene, 1-decene, 2-pentene, 2-hexene, 2-heptene, 2-octene, 3-hexene and 3-heptene.

9. A process according to claim 1 wherein said cobalt carbonyl complex is selected from the group consisting of cobalt carbonyl, hydrocobalt carbonyl and cobalt carbonyl complex obtained by substituting a part of carbonyl ligands with a pyridine base.

10. A process according to claim 1 wherein said pyridine base is selected from the group consisting of pyridine, 2-vinyl pyridine, 3-vinyl pyridine, 4-vinyl pyridine, 3-methyl-4-vinyl pyridine, α-picoline, β-picoline, γ-picoline, 4-ethyl pyridine and 3,5-dimethyl pyridine.

11. A process according to claim 1 wherein said hydroesterification reaction mixture is brought into contact with (a) pyridine or γ-picoline and (b) water in an inert gas, carbon monoxide gas or a water gas atmosphere under atmospheric pressure or higher pressure at an ambient temperature to 100° C.

12. A process for separating a cobalt component from a hydroesterification reaction mixture, comprising:

contacting a hydroesterification reaction mixture, obtained by reacting a polyhydric alcohol, an olefin, and carbon monoxide in the presence of a cobalt carbonyl complex and pyridine or γ-picoline wherein said pyridine or γ-picoline is present at a weight ratio of 0.5 to 5 to a fatty acid ester of said polyhydric alcohol obtained by said reacting, with water to separate said reaction mixture into two phases consisting of a phase containing said ester and a phase containing said cobalt component.

13. A process according to claim 12 wherein the weight ratio of water to pyridine or γ-picoline is 0.05 to 10.

* * * * *